US005681561A

United States Patent [19]
Hirshowitz et al.

[11] Patent Number: 5,681,561
[45] Date of Patent: Oct. 28, 1997

[54] COMPOSITIONS AND METHODS FOR IMPROVING AUTOLOGOUS FAT GRAFTING

[75] Inventors: Bernard Hirshowitz; Ella Lindenbaum; Yaron Har-Shai, all of Haifa, Israel

[73] Assignee: Life Medical Sciences, Inc., Princeton, N.J.

[21] Appl. No.: 475,543

[22] Filed: Jun. 7, 1995

[51] Int. Cl.$^6$ ................................................. A61K 35/12
[52] U.S. Cl. .................. 424/93.7; 424/574; 435/240.1; 435/240.2; 514/2; 514/21
[58] Field of Search ................... 424/93.7, 574; 435/240.1, 240.2; 514/321

[56] References Cited

U.S. PATENT DOCUMENTS

| | | | |
|---|---|---|---|
| 4,205,126 | 5/1980 | Cartaya | 435/2 |
| 4,940,666 | 7/1990 | Boyce et al. | 435/371 |

FOREIGN PATENT DOCUMENTS

| | | |
|---|---|---|
| 897760 A1 | 1/1984 | Belgium. |
| 9119480 A1 | 12/1991 | WIPO. |
| 9304691 | 3/1993 | WIPO. |
| 9304691 A1 | 11/1993 | WIPO. |

OTHER PUBLICATIONS

Petruschke et al., International Journal of Obesity and Related Metabolic Disorders 18(8): 532–536 (Aug. 1994).
Wabitsch et al., Metabolism 44(10): 45–49 (Oct. 1995).
Kern et al., Journal of Clinical Investigation 81: 398–406 (Feb. 1988).
Hauner et al., European Journal of Clinical Investigations 25: 90–96 (1995).
Zhang et al., Chung–Hua Cheng Hsing Shao Shang Wai Ko Chih (Chinese Journal of Plastic Surgery and Burns) 10(6): 440–443 (Nov. 1994).
Silkiss et al., Ophthalmic Plastic and Reconstructive Surgery 3(2): 71–75 (1987).
Hausman, Journal of Animal Science 67: 3136–3143 (1989).
Marques et al., Scandinavian Journal of Plastic and Reconstructive Surgery and Hand Surgery 28(4): 241–247 (Dec. 1994).
Eppley et al., Journal of Oral and Maxillofacial Surgery 50: 477–482 (1992).
Eppley et al., Aesthetic Plastic Surgery 15: 215–218 (1991).
Byron "Dispos-a-Ject System" brochure, 1991.
Byron "Toomey Aspiration Cannulas" brochure, 1991.
Byron "DTK" brochure, 1991.
Byron "Microinjection With The Toomey Tip System" brochure, 1991.
Grazer, "Body Contouring" pp. 3964–4029.
Moscona et al "Free–Fat Injections for The Correction of Hemifacial Atrophy," Plastic & Reconstructive Surg. Sep. 89, pp. 501–506.
Eppley et al "Bioactivation of Free Fat Transfers" Plastic & Recon. Sur., Dec. 92 pp. 1022–1030.
Jakoby & Pastan "Cell Culture" pp. 62–71.

*Primary Examiner*—Jean C. Witz
*Attorney, Agent, or Firm*—Henry D. Coleman; R. Neil Sudol

[57] ABSTRACT

The present invention relates to compositions and methods for enhancing the success of autologous fat grafting in a patient. The compositions according to the present invention are useful for enhancing autologous fat grafting by improving the survival rate of lipocytes which are injected into a patient as part of a fat grafting procedure. These compositions comprise a fat grafting effective amount of autologous lipocytes in combination with a lipocyte growth effective amount of a non-steroidal anabolic hormone selected from insulin, triiodothyronine/thyroxine ($T_3$ or $T_4$), mixtures thereof, and optionally, growth hormone, most preferably a mixture of all three hormones because of the favorable effect these three hormones exhibit in combination to promote autologous fat grafting, the hormones being further combined with a lipocyte growth effective amount of a nutrient medium, preferably a serum free nutrient medium as at least a minimum essential medium.

47 Claims, No Drawings

COMPOSITIONS AND METHODS FOR IMPROVING AUTOLOGOUS FAT GRAFTING

FIELD OF THE INVENTION

The present invention relates to compositions and methods for improving autologous fat grafting during surgical procedures and for cosmetic applications.

BACKGROUND OF THE INVENTION

Autologous fat is commonly used as a filler for depressions of the body surface. In a typical procedure, the fat is aspirated from the subcutaneous layer, usually of the abdominal wall by means of a suction syringe, and injected into the subcutaneous tissues overlying the depression.

It has been estimated empirically that only some (about 15-20%) of the injected fat survives and consequently the amount of fat injected is inexcess of that needed for filling the depression. Three, four or more fat injection procedures may be required before the desired goal of completely overcoming the depression is reached.

There are a number of explanations as to why so much of the injected fat is re-absorbed in the standard procedure. These reasons are described as being primarily mechanical, physiological or pathophysiological in nature. Mechanically, it is believed that the trauma incurred by the suction of the fatty aspirate, followed by its subsequent transfer to the injecting syringe, and the pressure exerted on the sample being injected through a narrow bore nozzle damages the fragile lipocytes (fat cells). Further, blood constituents, cell fragments and released proteolytic enzymes from the aspirate may produce an aseptic inflammatory reaction in the recipient site which will hinder the lipocyte "take". Physiologically, it is believed that the aspirate, injected in the form of aggregates of lipocytes, may not come into contact with nourishing body fluids, thus raising doubt as to the survival of the lipocytes in the center of the lipocyte aggregate. Pathophysiologically, it is believed that trauma associated with the depression to be treated may reduce the blood supply to the area, thus further prejudicing the "take" of the fat cells.

The rich blood supply of the head and neck makes this area a preferred recipient site for autologous fat grafting (AFG), with a higher expected likelihood of survival of fat cells than elsewhere in the body.

The plasmatic circulation for the initial take of a free skin graft extends over a period of about 72 hours. During this period, the nourishment for the grafted tissue is provided by diffusion of proteins, electrolytes, growth hormones, oxygen, etc. from the exudate of the recipient site. Thereafter, the capillary circulation takes over, with capillary buds growing into the free skin graft as the first step in the restoration of blood flow to the grafted tissue.

A similar progression of events may occur with autologous fat grafting (AFG) but the fragility of the cells and the poor penetration of nourishing body fluids into the inner lipocytes of the fat aggregates, weight against their take.

Following lumpectomy, an unsightly depression of the breast contour may cause distress to the patient. Autologous fat grafting (AFG) has been unsuccessful in such situations, perhaps because the breast comprises a good deal of fat tissue, which tissue is poorly supplied with blood vessels. Fat cells tend to find the breast tissue to be inhospitable for their survival.

Body prominences require padding of soft tissue to prevent sensitivity to pressure. Should this padding be lacking, the overlying skin may be adherent to the bone, leading to discomfort and even pain. In selected cases of this sort, autologous fat grafting could provide the interposition of the necessary padding.

According to present convention, depressions or hollows of the body surface associated with scarring are unlikely areas for a successful take of autologous fat grafting.

OBJECTS OF THE INVENTION

It is an object of the invention to provide a simple method for improving the survival rates of lipocytes during autologous fat grafting and the overall success rate for autologous fat grafting.

It is a further object of the invention to provide novel compositions for use in enhancing the success rate of autologous fat grafting.

It is still another object of the present invention to expand the use of autologous fat grafting to areas of the body previously considered unsuitable for such a technique.

These and other objects of the present invention may be readily gleaned from the description of the invention which follows.

BRIEF DESCRIPTION OF THE INVENTION

The present invention relates to compositions and methods which may be used to substantially enhance the success rate of autologous fat grafting. In addition, the present invention improves the survival rate of lipocytes which are used during autologous fat grafting and consequently, significantly enhances the likelihood that the lipocytes will take in such a procedure, thus reducing the number of injections of lipocytes which will be required to produce a successful graft.

The present invention relates to compositions and methods for enhancing the success of autologous fat grafting in a patient. The compositions according to the present invention are useful for enhancing autologous fat grafting by improving the survival rate of lipocytes which are injected into a patient as part of a fat grafting procedure. These compositions comprise a fat grafting effective amount of autologous lipocytes in combination with a lipocyte growth effective amount of a non-steroidal anabolic hormone selected from insulin, triiodothyronine/thyroxine ($T_3$ or $T_4$), mixtures thereof, and optionally, growth hormone, most preferably a mixture of all three hormones because of the favorable effect these three hormones exhibit in combination to promote autologous fat grafting, the hormones being further combined with a lipocyte growth effective amount of a cellular nutrient medium, preferably a serum free cellular nutrient medium as at least a minimum essential medium.

In preferred embodiments according to the present invention, the non-steroidal anabolic hormone is insulin. In further preferred embodiments, the compositions also include triiodothyronine ($T_3$), thyroxine or growth hormone along with insulin as the anabolic hormone. In most preferred embodiments according to the present invention, the anabolic hormone comprises a mixture of a fat grafting effective amount of insulin, growth hormone and triiodothyronine/thyroxine. Embodiments in which the anabolic hormone is a mixture of effective amounts of triiodothyronine/thyroxine and growth hormone or growth hormone and insulin are also contemplated by the present invention.

In general, insulin is included in compositions according to the present invention at concentrations ranging from about 5 ng/ml to about 100 ug/ml (preferably, at least about 50 ng/ml within this range), more preferably about 500 ng/ml to about 5 ug/ml (or slightly higher-up to about 10 ug/ml). It is noted that the amount of insulin as well as other components of the instant invention may be modified—generally according to the length of storage time prior to use (generally, the longer the storage time, the more hormone is added). When a non-steroidal anabolic hormone other than insulin is included in compositions according to the present invention, for example, triiodothyronine, thyroxine or human growth hormone, each hormone is included in an effective amount of at least about 0.05 ng/ml of the formulation, with a preferred range of about 0.5 ng/ml to about 100 ng/ml or more (generally, up to about 100 ng/ml or more in the case of thyroxine). In general, the anabolic hormone is included in concentrations based upon the general assumption that 1 ml of solution is approximately equal to about 1 gram in weight of the final composition. Percent weights may fall outside of these ranges, depending upon the amount of fat to be grafted, the size of the graft to be performed, the level of stability of the hormone and other factors, as well recognized by one of ordinary skill in the art.

In addition to insulin, the compositions according to the present invention generally include at least one anabolic hormone selected from triiodothyronine or thyroxine and growth hormone, most preferably both growth hormone and triiodothyronine or thyroxine. When growth hormone is used, the preferred growth hormone is human growth hormone, either with triiodothyronine ($T_3$) or preferably in combination with both insulin and triiodothyronine ($T_3$). The preferred amount of anabolic hormone other than insulin used will generally depend on the amount of fat to be used and the type of graft to be performed and/or the depression of the body surface to be filled, but generally and in most of the cases will be in the range of between about 0.5 ng/ml to about 100 ng/ml by weight or more of the composition. Of course, one of ordinary skill in the art will recognize that the addition of higher quantities of anabolic hormones (other than insulin-which is generally used in amounts up to about 100 ug/ml.) above 100 ng/ml may be used, especially where the compositions are to be used after a period of storage and the hormone included is known to degrade over that period of storage time (components used in the present invention may become less active over time).

Triiodothyronine ($T_3$) is generally preferred over thyroxine because it has greater potency and the same general activity as thyroxine. In instances where storage stability becomes a concern, the substitution of thyroxine ($T_4$) for triiodothyronine ($T_3$) in the compositions may be preferred. In cases where thyroxine is substituted for triiodothyronine, the amount of thyroxine included is generally about 3–5 times the amount of triiodothyronine used in order to provide the same relative degree of activity. Thus, while triiodothyronine may be included in compositions within a preferred concentration range of about 1.0 ng/ml to about 50 ng/ml, more preferably about 5 ng/ml to about 20 ng/ml, thyroxine is preferably included within a range of about 5 ng/ml to about 100 ng/ml or more, more preferably about 20 ng/ml to about 80–90 ng/ml.

DETAILED DESCRIPTION OF THE INVENTION

In describing the present invention in the specification, a number of terms will be used.

The term "autologous fat graft", "AFG" or "autologous fat implantation" is used throughout the specification to describe a graft using lipocytes taken from a patient to fill in depressions in the body of the same patient in an area of the body other than that site from which the lipocytes are taken or otherwise to augment tissue of a patient (external or internal). AFG is used to fill soft tissue deficit, for augmentation of external and internal surfaces and structures of the body such as in urological surgery, in reconstructive surgery and as an alternative to silicone or collagen fillers. AFG is used to fill depressions after injury or pursuant to surgical procedures such as cosmetic surgery, including facelifts, mastectomies or lumpectomies and related procedures to remove cancerous tissue, especially including tumors at or near the surface of the patient and in numerous other applications, including urological procedures involving the buildup of weak or damaged structural tissue.

The term "depression" is defined herein as an area of the body which is hollow or sunken and lacks the cellular substance, body or volume compared to the same area on a normal body. In essence, a depression represents an area where tissue has been removed, destroyed, injured, atrophied or is otherwise absent compared to a normal body. Depressions are smaller in size or are sunken relative to that same area in a normal body. Depressions in the body may result from the removal of tissue during surgery, the aging of tissue, disease, trauma or other injury. The compositions according to the present invention are useful in varying degrees for enhancing autologous fat grafting in any situation where the introduction and growth of lipocytes in the body would be desirable.

The terms "lipocytes", "autologous lipocytes", "adipose cells" and "adipocytes" are used to describe the fat storing cells which are taken from the body of a patient and used in the autologous fat graft according to the present invention. According to the present invention lipocytes are removed (generally, by suctioning) from subcutaneous fat layers in the area of the stomach, legs or other areas where significant fat cells may be found. Lipocytes which are removed from the patient and reintroduced into that patient during the autologous fat graft are substantially free of unrelated cells such as erythrocytes, other blood cells, fibroblasts and other cells which may contaminate the lipocytes. Significant contamination of lipocytes during autologous fat grafting may produce an aseptic inflammatory response which can produce scarring and contraction from the implantation and is generally associated with a poor success rate for autologous fat grafting. In one aspect of the present invention, compositions include effective amounts of lipocytes in combination with a cellular nutrient medium and at least one anabolic hormone.

In general, the number or concentration of lipocytes included in the autologous fat grafting compositions according to the present invention is that amount effective for producing an autologous fat graft. The term "fat graft effective amount" is used in conjunction with amounts or concentrations of lipocytes which are traditionally used in autologous fat graft procedures and are also used in the present invention. This number may vary over a wide range and one of ordinary skill in the art will recognize that this number will vary depending upon the type and size of the depression or area to be filled, the relative degree of vascularization of the area to be grafted, the age of the patient to be treated and the relative viability of the lipocytes isolated or removed from the patient. The number or concentration of lipocytes used in the present invention is that amount which attains a viscosity suitable for injection. In general, the concentration of lipocytes used in the present invention is that amount which is traditionally used in fat grafts. One of ordinary skill in the art is aware of the concentrations of lipocytes which are used in autologous fat grafting procedures. By way of reference, without being limited by way of desription, in general, the concentration of lipocytes included in the compositions according to the present invention will range from about $5 \times 10^6$ to about $5 \times 10^{12}$ lipocytes per mL., more preferably about $5 \times 10^8$ to about $5 \times 10^{10}$ lipocytes per ml. These ranges are generally approximately the same ranges which are used in traditional fat grafting procedures and are adjusted according to the procedure used, the site of injection, the relative vascularization of the site to be injected, the vascularization of the fat tissue removed and the density of the fat cell tissue source. One of ordinary skill in the art will recognize that certain conditions may necessitate the adjustment of the lipocyte concentrations outside of the above described ranges.

The term "lipocyte growth effective amount" is used throughout the specification to describe amounts or concentrations of components which, when used in the compositions according to the present invention, maintain and support or otherwise enhance the growth of lipocytes which are used in autologous fat graphs according to the present invention.

The term "separated" or "substantially separated" is used throughout the specification to describe lipocytes in preferred embodiments according to the present invention, wherein lipocytes which have been isolated from a patient and which will be used in an autologous fat graft are subjected first to a procedure to further separate the lipocytes from other components which may be found in the aspirated fat, such as, for example, triglycerides, lysozomes, other cellular fragments, blood components, blood cells and large connective tissue fragments, among other less desirable components, before use. For purposes of defining the present invention, the resulting lipocytes are considered separated or substantially separated from the other less desirable components. Any procedure to separate the lipocytes from these other non-lipocyte components may be used, but preferably, several centrifugation steps are employed.

The term "serum free cellular nutrient medium", "serum free cellular nutrient mixture" or "nutrient medium" is used throughout the specification to describe a medium or mixture (generally, at least a minimum essential medium) which contains no serum, and in combination with at least one anabolic hormone, preferably at least two or more anabolic hormones and optionally, at least one cellular growth factor or transforming factor comprises the wound healing compositions according to the present invention. The serum free nutrient medium according to the present invention is a minimum essential medium comprising the following elements: (a) essential amino acids (b) non-essential amino acids; (c) vitamins selected from the group consisting of folate, nicotinamide, pantothenate, pyridoxine, riboflavin, thiamin and mixtures thereof, preferably a vitamin mixture comprising a mixture of folic acid, nicotinamide, pantothenate, pyridoxine, riboflavin and thiamin; (d) glucose or nother equivalent carbon source such as galactose, among others; and (e) a mixture of inorganic ions selected from the group consisting of calcium, sodium, potassium, magnesium, chloride and mixtures thereof, preferably a mixture comprising calcium, sodium, potassium, magnesium and chloride. All of the elements (a), (c), (d) and (e) are necessarily included in a minimum essential medium according to the present invention along with the anabolic hormone. In addition, non-essential amino acids (b) are preferably included in the present compositions. Optionally, the cellular growth factor or transforming factor are also included. All of the elements are included in the medium in concentrations and/or amounts effective for maintaining the growth of lipocytes which are used in the autologous fat grafts of the present invention. The inclusion of non-essential amino acids pursuant to the present invention is clearly preferred. The preferred concentration of essential and optionally and preferably, non-essential amino acids used in the present invention ranges from about 5.0 um ($10^{-6}$ mole) to about 50 mmol. ($10^{-3}$ mole). The preferred concentrations of vitamins used in the present invention ranges from about 1 nanomole ($10^{-9}$ mol.) to about 10 um. The preferred concentrations of glucose or equivalent carbon source such as galactose used in the invention ranges from about 1 umol. to about 10 or more mmol. In the case of element (e), these inorganic ions are preferably included in the present compositions at a concentration range of about 1 umol to about 50 mmol.

In addition to the elements (a), (c), (d) and (e) and preferably (b), the nutrient medium according to the present invention optionally contains any one or more of at least one constituent within the following elements: (f) purines and pyrimidines (as the bases or nucleosides) such as adenine, guanine, cytosine, cytidine, deoxycytidine, thymine, thymidine, uracil and uridine, among others; (g) other organic compounds such as acetate, choline, i-Inositol, putrescine, pyruvate, linoleate and oleate, among others; (h) other inorganic ions such as phosphate and sulfate, among others; (i) trace elements such as copper, chromium, cobalt, iron, zinc, vanadium, tin, silicone, selenium, nickel, molybdenum, fluorine and iodine, among others; (j) buffers and indicators such as bicarbonate, carbon dioxide, phenol red and HEPES, among others; and (k) other supplements, for example, ethanolamine and phosphoethanolamine, among others.

All of the optional elements (f), (g), (h), (i), (j) and (k), when they are included in the nutrient medium according to the present invention, are included in amounts effective for maintaining the growth of lipocytes which are included in the compositions of the autologous fat grafts according to the present invention. Preferably, components (f), (g), (j) and (k) range in concentration from about 1 nmol. to about 10 mmol. In the case of components (h) and (j), the concentration preferably ranges from about 1 umol. (micromole) to about 50 mmol. One of ordinary skill in the art will be able to readily modify the type and amount of the components of the cellular nutrient medium as at least a minimum essential medium within the teachings of the present invention.

In addition to serum free cellular nutrient medium, the present invention may also make use of cellular nutrient medium containing serum, although the use of a serum containing cellular nutrient medium is generally less preferred than is serum free medium. Examples of such nutrient medium include, among numerous others DMEM, HAM F12 and HAM F10, all containing serum. The term "cellular nutrient medium", "nutrient medium" or "nutrient mixture" is used to describe all types of nutrient medium contemplated for use in the present invention which contain at least the basic elements (generally, at least those of a minimum essential medium) as described hereinabove, and such term includes serum free cellular nutrient medium. It is noted that serum from the patient undergoing an autologous graft may be present at the recipient site, but this endogenous serum is not considered with reference to the description of the nutrient medium pursuant to the present invention.

The cellular nutrient medium according to the present invention may include one or more commercially available media in solution or lyophilate (solid) form. The cellular nutrient medium used may be in the form of a lyophilate which is reconstituted with water, preferably sterilized, distilled water prior to use and then supplemented with an anabolic hormone (the anabolic hormone itself optionally in lyophilate form) such as insulin, triiodothyronine, thyroxine, growth hormone or mixtures thereof, and optionally, a cellular growth factor or transforming factor or other additive. Alternatively, the nutrient medium may be used directly in formulations according to the present invention in the form of a solution, or may be formulated first as a lyophilate before being reformulated as a solution prior to use.

Many of the commercially available media (preferably, serum free) are available from suppliers such as Collaborative Research Incorporated, Bedford Mass., GIBCO, Grand Island, N.Y., USA or Biological Industries, Beth HaEmek, Israel. These media may be used as purchased or modified within the scope and practice of the present invention.

The term "non-steroidal anabolic hormone" is used throughout the specification to describe the primary hormones which are included in the instant invention to promote the growth of lipocytes and enhance the likelihood of successful autologous fat graft in combination with the cellular nutrient media (at least a minimum essential medium). These primary hormones include insulin, triiodothyronine, thyroxine, and growth hormone among others. When growth hormone is used, it is preferred to use it in combination with triiodothyronine/thyroxine or insulin or most preferably with a mixture of triiodothyronine/thyroxine and insulin. As used herein, the term non-steroidal anabolic hormone includes naturally isolated (preferably, human) or synthetically produced versions of these hormones which are known to function substantially the same as the naturally occuring hormones and includes, where relevant, compounds produced by genetic engineering processes and techniques. Insulin is a preferred non-steroidal anabolic hormone. While not being limited by way of theory, it is believed that the inclusion of at least one non-steroidal anabolic hormone selected from insulin and triiodothyronine or thyroxine, and preferably at least two or more anabolic hormones selected from insulin, triiodothyronine or thyroxine and growth hormone, serves to enhance the effect of the nutrient media in enhancing the growth of lipocytes which are administerd during the autologous fat graft pursuant to the present invention. Thus, it is believed that the non-steroidal anabolic hormone actually enables the lipocytes to utilize or process the nutrients in the media in order to promote their growth, which action results in an increased likelihood of success of the fat implantation.

The term "cellular growth factor", "cellular transforming factor" or "transforming factor" is used throughout the specification to describe those compounds other than the anabolic hormones which may be optionally added to the formulations according to the present invention for their known benefits in stimulating the growth and elaboration of cells. Cellular growth factors or transforming factors for use in the present invention include for example, epithelial growth factor (EGF), platelet derived growth factor (PDGF), transforming growth factor (TGF) and insulin-like growth factor (IGF), among others. In certain formulations according to the present invention, one or more cellular growth factor or transforming factor may be included in combination with at least one anabolic hormone, most preferably a combination of effective amounts of insulin, triiodothyronine and growth hormone in an amount effective for maintaining or enhancing the growth of fat cells which have been injected as part of the autologous fat graft. Cellular growth factors or transforming factors for use in the present invention may include naturally isolated or synthetically produced versions of the above-mentioned compounds or their equivalents and include, where relevant, compounds produced by genetic engineering processes and techniques.

The amount of each component which is used in the formulations according to the present invention will depend upon the type and size of the graft to be performed and the number of lipocytes injected during the grafts, but each component preferably is included in an amount effective for maintaining and/or enhancing the growth of autologous lipocytes which are injected into a patient, which in turn, increases the likelihood of the success of the autologous fat graft pursuant to the present invention. In general, in embodiments according to the present invention, the formulations include an anabolic hormone other than insulin at an effective concentration for enhancing the growth of autologous lipocytes of at least about 0.05 ng/ml, preferably about 0.5 ng/ml to about 100 ng/ml or more, more preferably about 0.5 ng/ml to about 100 ng/ml.

In the case of formulations containing insulin, the amount of insulin generally falls outside of and above this range, because of its tendency to degrade and become inactivated at a more rapid rate than the other anabolic hormones. Stabilized forms of insulin could obviously be used as a substitute of insulin. Preferably, the anabolic hormone is insulin or insulin and at least one other hormone because of the benefits these hormones have in promoting the growth and elaboration of cells and their general absence of toxicity.

The preferred anabolic hormone is insulin in combination with either triiodothyronine, thyroxine or growth hormone. The preferred insulin is human insulin, which is a well-known protein which is readily available commercially from a number of sources (for example, Sigma Chemical Co., USA or Novo Nordisk, Copenhagen, Denmark). It is constituted from a number of amino acids (approximately 51) with a total molecular weight of about 5,500. Human insulin for use in the present invention is generally prepared using genetic engineering techniques. Depending upon the manufacturer, the insulin may have slightly different activity based upon weight, however the activity of insulin defined in units is, of course, standard. While not being limited by way of theory, in the present invention, it is believed that the insulin promotes the growth of lipocytes by enhancing the transport and utilization of glucose by the cells.

Growth hormone may also be used in the present invention, either alone or preferably in combination with insulin or triiodothyronine/thyroxine and most preferably in combination with both triiodothyronine/thyroxine and insulin. The preferred human growth hormone is a well-known defined protein which is readily available and results from a pituitary secretion into the blood system. It is constituted from a number of amino acids with a total molecular weight of about 193,000. The human growth hormone which may be used in the present invention can be obtained from a variety of sources, including genetic engineering processes and techniques. While not being limited by way of theory, it is believed that the growth hormone stimulates fibrinogenesis, i.e., the synthesis of growth factors which also may exhibit some favorable influence on the rate of growth of lipocytes.

The present invention also contemplates the inclusion of effective amounts of triiodothyronine/thyroxine either alone or in combination with other non-steroidal anabolic hormones. The preferred triiodothyronine is human triiodothyronine, which is a well-known defined hormone and readily available commercially. Triiodothyronine and thyroxine are naturally occurring amino acids of the thyroid gland which exert a stimulating effect on metabolism. Although virtually identical in metabolic effects, triiodothyronine is more potent than is thyroxine and is preferred for use in the present invention. While not being limited by way of theory, it is believed that the triiodothyronine or thyroxine utilized in the present invention stimulates vascularization and facilitates the resupply of blood borne components. It is further believed that $T_3$ and $T_4$ may promote the dissociation of oxygen from hemoglobin and may also contribute to tissue growth and regeneration by making oxygen more readily available.

A particularly preferred composition according to the present invention comprises a mixture of an effective amount of human growth hormone in the presence of an effective amount of insulin (transferrin containing or transferrin-free) and triiodothyronine ($T_3$) or thyroxine ($T_4$), preferably in a serum free cellular nutrient medium (at least a minimum essential medium). In this preferred embodiment of the instant invention, the anabolic hormones other than insulin, i.e., growth hormone and/or triiodothyronine/ thyroxine are generally included in the final composition in a concentration range of about 0.05 ng/ml to about 100 ng/ml or more, preferably about 0.5 ng/ml to about 100 ng/ml. In this preferred embodiment, insulin is also included in an effective amount, generally an amount which is substantially greater than the other anabolic hormones because of its tendency to rapidly degrade or become inactive over time. The amount of insulin is preferably included in amounts ranging from about 5 ng/ml to about 100 ug/ml (preferably, at least about 50 ng/ml within this range), preferably about 500 ng/ml to about 5 ug/ml (or slightly higher-up to about 10 ug/ml). One of ordinary skill in the art will know to vary the amount of anabolic hormones within effective ranges based upon the type and potency of the preparation of the compound.

The present invention may also optionally include a cellular growth factor or transforming factor in addition to one or more non-steroidal anabolic hormones. Each cellular growth factor or transforming factor is included in the final composition in an effective amount to enhance the growth of lipocytes, i.e., an amount generally ranging from about 0.05 to about 50 ng/ml or higher concentration, and preferably about 1 ng/ml to about 20 ng/ml or more of the final composition.

The nutrient medium which is used in the present invention is any nutrient medium having the effect of providing a favorable environment for growing lipocytes in an autologous fat graft when used in combination with the non-steroidal anabolic hormone. In preferred embodiments according to the present invention, the nutrient media comprised of the componentry set forth hereinabove, is mixed with an effective amount of the non-steroidal anabolic hormone in combination with a fat graft effective amount (number) of autologous lipocytes to form the compositions according to the present invention.

The cellular nutrient medium preferably comprises effective amounts of the following constituents: (a) essential amino acids; (b) non-essential amino acids; (c) vitamins as previously described; (d) inorganic ions as previously described and (e) glucose; and optionally, (f) purines and pyrimidines; (g) other organic compounds; (h) other inorganic ions; (i) trace elements; (j) buffers and indicators and (k) other supplements. It is noted that in certain instances non-essential amino acids may be eliminated from the formulations, but these compositions are less preferred. Preferably, the cellular nutrient medium used herein contains effective amounts of elements (f) through (k). Serum free nutrient medium is preferred. The preferred serum free nutrient medium is modified MCDB, in particular, MCDB 105, a well-known medium. Mixtures of standard commercial nutrient media may also be used with favorable results in the instant invention.

While not being limited by way of theory, it is believed that one plausible explanation of the mechanism of the fat graft enhancement is that the presence of the anabolic hormone, and in particular, insulin and/or triiodothyroine/ thyroxine and/or human growth hormone (preferably a mixture of at least two of these anabolic hormones and most preferably a combination of insulin, triiodothyronine or thyroxine and growth hormone) in the formulations according to the present invention, promotes the utilization of the nutrients from the nutrient medium and consequently, growth in situ of injected lipocytes, within the area of the body where the graft is performed. At the same time, the present formulations may also induce the stimulation of the vascular elements and promote the vascularization of the lipocytes which are injected as part of the grafting process, thus making a sucessful outcome that much more likely. While not being limited by way of theory, the mechanism which might be assumed is that during the proliferation phase after the autologous fat graft has been performed, new capillaries may appear in the fat cells, thus promoting further elaboration and growth of the fat cells. The new vessels may originate as budlike structures on nearby vessels, penetrate the body of lipocytes, thus making the graft successful.

It is further believed that the function of the nutrient medium is to provide nutrients to the lipocytes to prolong their life at the site of the graft during the period between cell aspiration and neovascularization of the injected cell mass. This is believed to enhance the likelihood that the graft will be successful. In this way, the nutrient medium functions with the non-steroidal anabolic hormone to promote the normal processes of elaboration, vascularization and growth of the fat graft and the adjacent tissue areas.

A number of nutrient media, preferably serum free, alone or in combination, may be used in the present invention, including commercially available media or other media well known in the art. Examples of such media (all without serum or having had the serum removed) include Minimum Essential Medium Eagle, ADC-1, LPM (Bovine Serum Albumin-free), F10 (HAM), F12 (HAM), DCCM1, DCCM2, RPMI 1640, BGJ Medium (with and without Fitton-Jackson Modification), Basal Medium Eagle (BME-with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E- with Earle's salt base), Medium M199 (M199H- with Hank's salt base), Minimum Essential Medium Eagle (MEM-E- with Earle's salt base), Minimum Essential Medium Eagle (MEM-H- with Hank's salt base) and Minimum Essential Medium Eagle (MEM-NAA- with non-essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the present invention is MCDB 105. These and other useful serum-free nutrient media are available from GIBCO, Grand Island, N.Y., USA and Biological Industries, Bet HaEmek, Israel, among others. A number of these media are summarized in *Methods in Enzymology*, Volume LVIII, "Cell Culture", pp. 62–71, edited by William B. Jakoby and Ira H. Pastan, published by Academic Press, Inc.

In addition, serum-containing nutrient media may also be used in compositions according to the present invention, but the use of serum-containing media is less preferred because of the possibility that the serum may be contaminated with microbial agents and because the patient may develop immunological reactions to certain antigenic components contained in the serum. In addition, serum-containing media tends to be undefined and much more difficult to reproduce. It is noted, however, that serum associated with the tissue taken as the source of autologous lipocytes from the patient may find its way into the final compositions according to the present invention.

While a large number of serum free nutrient media may be used in the present invention, a preferred nutrient media for use in the present invention is modified MCDB 105.

Clinical experiments which were carried out to prolong the viability of autologous fat grafts in humans showed that the use of the modified MCDB 105 medium in compositions according to the present invention, extended the limit of viability of the fat graft and improved the likelihood of a successful graft significantly.

Hereafter are enumerated the particular constituents and concentrations of the above groups for the preferred medium, MCDB 105:

| | Concentration in M |
|---|---|
| Group (a): | |
| Arginine | $1.0 \times 10^{-3}$ |
| Cysteine | $5.0 \times 10^{-5}$ |
| Glutamine | $2.5 \times 10^{-3}$ |
| Histidine | $1.0 \times 10^{-4}$ |
| Isoleucine | $3.0 \times 10^{-5}$ |
| Leucine | $1.0 \times 10^{-4}$ |
| Lysine | $2.0 \times 10^{-4}$ |
| Methionine | $3.0 \times 10^{-5}$ |
| Phenylalanine | $3.0 \times 10^{-5}$ |
| Threonine | $1.0 \times 10^{-4}$ |
| Tryptophan | $1.0 \times 10^{-5}$ |
| Tyrosine | $3.0 \times 10^{-5}$ |
| Valine | $1.0 \times 10^{-4}$ |
| Group (b): | |
| Alanine | $1.0 \times 10^{-4}$ |
| Asparagine | $1.0 \times 10^{-4}$ |
| Aspartate | $1.0 \times 10^{-4}$ |
| Glutamate | $1.0 \times 10^{-4}$ |
| Glycine | $1.0 \times 10^{-4}$ |
| Proline | $3.0 \times 10^{-4}$ |
| Serine | $1.0 \times 10^{-4}$ |
| Group (c): | |
| Biotin | $3.0 \times 10^{-8}$ |
| Folinic acid | $1.0 \times 10^{-9}$ |
| Alpha-Lipoate | $1.0 \times 10^{-8}$ |
| Niacinamide | $5.0 \times 10^{-5}$ |
| Pantothenate | $1.0 \times 10^{-6}$ |
| Pyridoxine | $3.0 \times 10^{-7}$ |
| Riboflavin | $3.0 \times 10^{-7}$ |
| Thiamin | $1.0 \times 10^{-6}$ |
| Vitamin B12 | $1.0 \times 10^{-7}$ |
| Group (d) | $4.0 \times 10^{-3}$ |
| Glucose | |
| Group (e): | |
| Magnesium | $1.0 \times 10^{-3}$ |
| Potassium | $3.0 \times 10^{-3}$ |
| Sodium | $1.3 \times 10^{-1}$ |
| Chloride | $1.2 \times 10^{-1}$ |
| Calcium | $1.0 \times 10^{-3}$ |
| Group (f): | |
| Adenine | $1.0 \times 10^{-5}$ |
| Thymidine | $3.0 \times 10^{-7}$ |
| Group (g): | |
| Choline | $1.0 \times 10^{-4}$ |
| i-Inositol | $1.0 \times 10^{-4}$ |
| Putrescine | $1.0 \times 10^{-9}$ |
| Pyruvate | $1.0 \times 10^{-3}$ |
| Linoleate | $1.0 \times 10^{-8}$ |
| Group (h) | |
| Phosphate | $3.0 \times 10^{-3}$ |
| Sulfate | $1.0 \times 10^{-3}$ |
| Group (i): | |
| Cobalt | $1.0 \times 10^{-7}$ |
| Copper | $1.0 \times 10^{-9}$ |
| Iron | $5.0 \times 10^{-6}$ |
| Manganese | $1.0 \times 10^{-9}$ |
| Molybdenum | $7.0 \times 10^{-10}$ |
| Nickel | $5.0 \times 10^{-10}$ |
| Selenium | $3.0 \times 10^{-8}$ |
| Silicon | $5.0 \times 10^{-7}$ |
| Tin | $5.0 \times 10^{-10}$ |
| Vanadium | $5.0 \times 10^{-9}$ |
| Zinc | $5.0 \times 10^{-7}$ |
| Group (j): | |
| HEPES | $3.0 \times 10^{-2}$ |
| Phenol Red | $3.3 \times 10^{-6}$ |

Weights of each of the above components in the medium may be varied within the concentrations described hereinabove to provide formulations workable within the description of the present invention.

Preferably, the non-steroidal anabolic hormone to be incorporated into the modified MCDB 105 composition, according to the present invention, is a mixture of two hormones selected from insulin, triiodothyronine/thyronine and growth hormone at effective concentrations. Most preferably, the anabolic hormone includes a mixture of human growth hormone, insulin (containing transferrin or transferrin-free) and triiodothyronine ($T_3$) or thyroxin ($T_4$), each hormone included in a lipocyte growth effective amount. Hormones other than insulin are included in an amount ranging from at least about 0.05 ng/ml, preferably at least about 0.5 ng/ml to about 100 ng/ml. In the case of thyroxine, this anabolic hormone is preferably included in amounts ranging from about 5 ng/ml to about 100 ng/ml. In the case of insulin, the effective amount of insulin generally ranges from about 5 ng/ml to about 100ug/ml (preferably, at least about 50 ng/ml within this range) and more preferably about 500 ng/ml to about 5 ug/ml (or slightly higher-up to about 10 ug/ml) within this range. Higher amounts of insulin may be merited where the formulation is to be stored for longer periods of time.

In addition to lipocyte growth effective amounts of non-steroidal anabolic hormones and cellular nutrient media and optionally, effective amounts of at least one cellular growth factor or transforming factor, formulations according to the present invention may also advantageously contain ascorbic acid, which in certain instances may have a beneficial overall effect in maintaining and/or enhancing the growth of lipocytes because of ascorbic acid's ability to function as a reducing agent. Transferrin (which is believed to improve iron transport) in amounts which preferably range from about 500 ng/ml to about 50 ug/ml, more preferably about 5 ug/ml and selenite (preferably, in the form of sodium selenite) in amounts preferably ranging from about 0.5 to about 50 ng/ml, more preferably about 5 ng/ml, may also be optionally included in the present formulations.

Insulin (including transferrin or transferrin-free) is a desirable constituent anabolic hormone, found to impart a maturing stimulus for the growing culture. In addition, insulin is suitable for differentiation of lipocytes, induces fibroblasts to take up free lipid and become lipocytes and may retard lipolysis by adding 35 ug/ml to fat tissue in vitro. Insulin may be commercially obtained and is generally provided in mU quantities (about 41 ng of insulin). The International Unit of Insulin (SI=System International) is the activity contained in 0.04167 mg (41.67 ug) of the 4th International Standard Preparation (1958). The Standard Preparation is a quantity of purified Zinc Insulin crystals extracted 52% from Bovine and 48% from Porcine pancreas (See, Martindale Pharmacopoeia, 26th Ed.).

In a methodology for using the present invention, lipocytes are first removed from an individual to be treated by a standard liposuction process. Lipocytes are obtained, for example, from a small or large subcutaneous area containing fat cells. Preferably, lipocytes are removed from subcutaneous areas of the legs, buttocks or stomach, as these areas tend to have the fat of greatest density suitable for grafting, however, lipocytes may be removed from virtually any area of the patient to be treated. In removing lipocytes from the patient, a stable wound is first made into the fatty tissue, and the fat tissue is aspirated to remove fatty tissue. This aspiration step may be performed by any method suitable in the art. In this aspiration step, sufficient fatty tissue is removed in order to obtain lipocytes for a fat grafting procedure. One preferred aspiration system which may be used to remove lipocytes from a fat area of the body is the Toomey Aspiration System, available from Byron Medical, Tucson, Ariz. using Toomey Aspiration Cannula, 3–4 mm in diamter.

After aspiration and collection, the removed fatty tissue is collected and preferably separated from other undesirable components of the fatty tissue. This does two things. The first is that the lipocytes are now separated from other components which may reduce the likelihood of a successful "take" of the graft. The second is that the separation breaks up fat aggregates, thus making it more likely that the enriched medium will come into contact with more lipocyte cells in the fat sample to be grafted.

In order to separate the lipocytes, the collected fatty tissue is suspended in approximately equal volumes of nutrient medium (the volume to volume ratio may practically range from 1:3 to about 3:1, with a preferred ratio of about 1:1). Thereafter, the fatty tissue is centrifuged to remove cellular material such as fragments and debris, medium and blood components and blood cells and large connective tissue fragments. In addition, the fat aggregates are broken up, thus making it more likely that the enriched medium will exhibit its effect on more cells in the sample. Generally, centrifugation is performed for several or more minutes (up to about 10 or more minutes) at a centrifugation speed sufficiently fast to separate the lipocytes from the non-lipocyte material.

Centrifugation generally is performed on the fatty tissue at centrifugation speeds effective to separate the lipocytes from blood cell components, other cellular fragments, blood cells and large connective tissue fragments. Centrifugation speeds up to 1000× g are generally used in this step. A preferred centrifugation step is performed for 5 minutes at 200× g (about 1,000 rpm). Upon centrifugation, 4 phases are generally obtained:

1. The uppermost/lightest phase- consisting of a yellowish/clear thin layer of triglycerides, lysozomes and other cell fragments;
2. The upper-intermediate phase- a thick yellow to white colored layer consisting of the lipocytes cell mass;
3. The lower intermediate floatation medium phase which is a pink to red colored liquid consisting of the medium and blood components;
4. The lowermost sedimentation phase- a dark red phase consisting of blood cells and large connective tissue fragments.

After the initial centrifugation step, the uppermost phase is removed (pipette, aspiration, among other methods) and the lower intermediate floatation medium phase and the lowermost sedimentation phase are separated (e.g., aspirated with pipette or syringe, among other methods) from the desirable upper-intermediate phase containing lipocytes (the second layer). Care is taken to avoid breakage of the cell mass.

The lipocyte phase separated in this or an equivalent manner may be used directly in an autologous fat grafting procedure, or alternatively and preferably, this lipocyte phase is resuspended in nutrient medium and additionally centrifuged at least once and preferably at least two or three more times. After each centrifugation step, the remaining lipocyte layer is resuspended in nutrient medium. The lipocyte layer is purified in this manner until the medium is clear and the lipocytes are homogeneous in texture and color.

After separation, the lipocyte cell mass obtained is resuspended in fresh medium (generally, depending on the cenconcentration and final viscosity of the separated lipocytes, at a volume to volume ratio of about 5:1 to 1:5, preferably about 3:1 to about 1:3 and more preferably about 2:1 to about 1:1, most preferably about 2:1) and the mixture is injected into the deficit area where it is preferably distributed throughout the entire deficit space. A preferred injection system for use in the present invention to inject the present compositions into the deficit area is the Toomey Micro-Injection System or Dispose-A-Ject™ system, available from Byron Medical, Tucson, Ariz..

All centrifugation steps are preferably run at or near room temperature. The estimated time for the preparation of the injectable fat aspirate is approximately 10–15 minutes and the method may be easily learned and performed by a medical technician, for example, an operating theatre nurse.

The formulations as described hereinabove are added to effective amounts of the lipocytes which are injected into the tissue deficit in order to perform the autologous fat graft. The amount of enriched medium which is added to the lipocytes is that amount which will maintain the growth of the lipocytes which are used in the grafts. This amount is associated with the significant enhancement of the success of the autologous fat graft. The number of fat grafts which may be performed on a particular tissue deficit will generally range from one injection up to four or more injections. The number and concentration of lipocytes as well as to the total amount of lipocyte-containing formulations used in the autologous fat graft according to the present invention may be readily determined by one of ordinary skill in the art and will range depending upon the size and depth of the tissue deficit to be filled and/or the type of fat graft to be performed (area of the body to be filled). One of ordinary skill in the art will readily be able to determine the amount and frequency of administering the lipocyte-containing formulations according to the present invention.

Preliminary animal experiments and clinical trials to determine the relative efficacy of the present invention in enhancing the success of autologous fat grafts which were carried out on rats and on selected clinical cases indicated that the formulations according to the present invention exhibited a significant beneficial result relative to tradition autologous fat methodologies.

The invention will be described hereinafter by a number of Examples which illustrate some actual grafts carried out on with the compositions according to the present invention. It should be understood that the Examples are not exhaustive nor limiting and are presented only for a better understanding of the invention.

EXAMPLES 1–9

In the following examples 1–9, MCDB 105 was supplemented with non-steroidal anabolic hormones and tested for its effect in enhancing autologous fat grafting methodologies. The medium was prepared using MCDB 105 which was supplmented with growth hormone, insulin, thyroxine and calcium chloride and used as a solution.

Materials and Methods:

Enriched Medium

Enriched medium was prepared from 100 ml of MCDB 105 supplemented with growth hormone (5 ng/ml), insulin (5 micrograms/ml), thyroxine (77.7 ng/ml or $10^{-7}$M) and calcium chloride (147 ng/ml or 0.1 mM).

Equipment

For Aspiration:

Toomey Aspiration System (Byron Medical, Tucson, Ariz.)

Toomey Aspiration Cannula 3–4 mm internal diameter.

For Reintroduction or Injection of Lipocytes:

Dispos-A-Ject™ System (Byron Medical)

Vacuum of 1 atmosphere pressure.

Centrifuge—Hettich Type 2001

Methodology

Make stab wound, insert cannula into the subcutaneous donor site and pull the plunger back until locked into place by the snapper. Aspirate what is needed and remove the cannula from the wound site.

Preparation of Subcutaneous Fat

Place collected subcutaneous fat into 15 ml sterile test tubes and suspend the lipocytes in an equal volume of the enriched medium, prepared above. Centrifuge the lipocyte mixture specifically for 5 minutes at 1,000 rpm or approximately, 200× g (up to 10 minutes at up to 1000× g). The following four phases are obtained:

1. The uppermost, lightest phase—a yellowish thin layer consisting of triglycerides, lysozomes and other cell fragments;
2. The upper-intermediate phase—a thick yellow to white colored layer consisting of the desirable lipocyte cell mass;
3. The lower intermediate floating medium phase—a pink to red colored liquid consisting of the medium and blood components; and
4. The lowermost sedimentation phase—a dark red phase consisting of blood cells and large connective tissue fragments.

After initial centrifugation, the uppermost, lightest phase (1) is removed using a sterile Pasteur pippette. Thereafter, aspirate the lower intermediate floatation medium phase (3) and the lowermost sedimentation phase (4) using a sterile Pasteur pippette which is slid along the wall of the test tube avoiding breakage of the cell mass. The remaining middle phase of the lipocyte cell mass is then resuspended in an equal volume of fresh medium.

The centrifugation, aspiration of the floatation medium and any remaining debris and resuspension steps are repeated 2–3 times until the medium is clear and the cells are homogeneous in texture and color. After resuspension in fresh medium (2:1 volume to volume, lipocytes to medium), the mixture is introduced into the Toomey Micro-Injection System (Dispos-a-Ject™) using a 14G needle, injected into the deficit area where it is distributed throughout the entire deficit space. The estimated time for the preparation of the injectable fat aspirate is about 10–15 minutes and the technique is easily applied by a technician.

EXAMPLE 1

ANIMAL EXPERIMENTS

Seventeen Wistar rats weighing between 250–300 grams were used. Eight animals were used as the experimental group and nine animals were used as controls. In both groups, segments of 0.5–1.0 gm. of subcutaneous fat were extirpated from the inguinal region. In the experimental group, under sterile conditions, the fat was placed in liquid enriched medium as prepared above and cut into 2 mm fragments under a Nikon dissecting microscope. It was then transferred into fresh enriched medium (1:1 v:v) and injected through a 2.5 mm gauge needle into the subcutaneous plane of the scalp between the ears. In the control group, the same procedure was followed using saline instead of enriched medium.

After 2 months the skin over the implant was opened and the implant was examined the skin over the implant was opened and the implant was examined under the microscope for vascularity and incapsulation. From each of the implants a section was cut and prepared for histological examination.

All the tissues of the experimental group revealed a highly vascularized fat pad with no tissue and no encapsulation. In the control group most of the fat was resorbed leaving scar tissue. Histological examination revealed that all of the experimental segments were composed of richly vascularized adipocytes while the control group was composed of adipocytes in different stages of resorption, extensive collagenous connective tissue which was dispersed througout.

CLINICAL TESTING

EXAMPLE 2

CASE HISTORY 1

A 62 year old male patient with a history of tumor of the brain underwent operations in Hadassah and in Switzerland. He was left with severe depression of the left temple region, and since he is restricted from gaining weight, only limited amount of fat was aspirated.

During the first operation he received an injection of 15 ml of aspirated fat cells. No addition of medium or isolation of the cells was performed. Overcorrection was performed but still severe resorption occurred. There was resorption of 75–80% of the injected fat cells.

The second operation took place later that year. This time the enriched medium was added to the fat cells, but only 6–8 ml was aspirated from the patient's abdomen. The take was 60–70% and the present appearance is fairly satisfactory. The patient consulted with another plastic surgeon who advised insertion of silicone semi-solid block, Silastic Brock soft (Dow Corning, Midland, Mich., Cat. No. 801), similar to reconstruction used in temporalis muscle for Bell's Palsy surgical procedure. However, the use of silicone being currently controversial, did not appeal to the patient and he chose to utilize the method according to the present invention.

EXAMPLE 3

CASE HISTORY 2

A female patient aged 66 had a history of trauma where she fell and bumped her forehead. This resulted in a depression of 2 cm×2.5 cm and a depth of 0.5 cm. Reconstructive surgery was performed. Two and one half ml. of fat cells were washed with medium and sieved through a gauze. The cells were then injected into the defect. Overcorrection was performed in anticipation of absorption but it did not reabsorb, therefore the patient was left with a lump that has to be corrected by aspiration.

EXAMPLE 4

CASE HISTORY 3

A female patient aged 24 sustained a multiple trauma during a road accident. The trauma included a severe fracture of the pelvic girdle which necessitated lying in bed in traction for a long period of time. She developed a sacral pressure sore which was closed primarily by suturing. She also developed difficulty in sitting because the sacrum was covered by scarred skin without any padding of subcutaneous fat.

She was operated on early the following year and 25 ml of fat was aspirated from the lower abdomen. The fat was washed in medium sieved through gauze and washed again in medium, then reinjected into the subcutaneous area. Overcorrection was performed and only 30% reabsorption occurred, yielding very satisfactory results with relief of the previous symptoms.

EXAMPLE 5

CASE HISTORY 4

A female patient in her late 50's had a radical mastectomy performed in early 1991. There was adequate skin for reconstruction of the breast with a breast implant- Silicone gel (Siltex, Mentor). She was left with a deep hollow in the left axilla, which was accentuated by the placement of the breast implant. Almost two years later, she had this hollow filled with an injection of subcutaneous fat taken from the lower abdomen. About 35 ml was injected in bulk without enriched medium being present. The result was virtually complete reabsorption of the fat.

A second operation was performed over a year later and this time enriched medium according to the present invention was added and the cells were washed twice and sieved through gauze. About 35 ml were injected by distributing the injected fat throughout the hollow space. Overcorrection was performed. In follow-up after 9 months, she has exhibited satisfactory results with minimal reabsorption.

EXAMPLE 6

CASE HISTORY 5

A 38 year old patient had severe multiple facial injuries sustained in an automobile accident in 1991. Reconstructive surgery was performed in early November and a segment of fat was cut into small segments of about 3 mm diameter, mixed with medium and reinserted into the depression on the outer side of the lateral angle of the eye.

In a follow-up visit after 4 weeks, no reabsorption was evident.

EXAMPLE 7

CASE HISTORY 6

A 24 year old female patient sustained localized third degree burns from an electrical applicance on the medial aspect of the left thigh, just above the knee joint. She was left with a depression and scar. The depression was about 7.5 cm×6 cm×1 cm depth.

Corrective surgery was performed and 35 ml of pure fat was aspirated from the left lower abdominal wall, suspended in enriched medium and centrifuged 5 min. at 2000 rpm (300× g). The 1st, 3rd and 4th phases were aspirated and the cells were resuspended, mixed, centrifuged and again Phase 1, 3 and 4 were aspirated. Then the fat was resuspended for the 3rd time and this mixture was injected into the tissue deficit.

EXAMPLE 8

CASE HISTORY 7

An 18 year old female patient was born with a left-sided hemifacial microsomia. At age 14 she underwent mandibular lengthening by oral surgeons. Thereafter 3 fat injections were performed to augment the soft tissue deficit in her left cheek.

Resorption of the injected fat was noticed up to 50%, but some filling remained. In order to preserve the syummetrical contour of her face, another fat inejction procedure was undertaken. In this procedure, the fat cells were sucked from the patient's medical thighs, suspended in enriched media and centrifuged. After centrifugation, the lipocytes were isolated and resuspended again in the media, centrifuged again and the isolated lipocytes (a total of 15 cc) were injected under hand pressure into the tissue deficit.

EXAMPLE 9

CASE HISTORY 8

A 40 year old male with bilateral gynecomastia was operated on for correction of the tissue defect. Overcorrection was undertaken which left him with severe depressions around the nipple area, more of the left side.

Recently, fat treated with enriched medium according to the present invention was injected into the tissue depressions. 35 cc of lipocytes containing enriched medium was injected into the left side of the deficit and and 15 cc into the right side.

This invention has been described in terms of specific embodiments set forth in detail herein, but it should be understood that these are by way of illustration and the invention is not necesarily limited thereto. Modifications and variations will be apparent from the disclosure and may be resorted to without departing from the spirit of the inventions those of skill in the art will readily understand. Accordingly, such variations and modifications are considered to be within the purview and scope of the invention and the following claims.

We claim:

1. A composition for use in autologous fat grafting procedures comprising an adipocyte growth effective amount of at least one anabolic hormone selected from insulin, triiodothyronine, thyroxine or mixtures thereof in combination with a nutrient medium comprising adipocyte growth effective amounts of essential amino acids, a mixture of vitamins comprising effective amounts of folate, niacinamide, pantothenate, pyridoxine, riboflavin and thiamin, a mixture of inorganic ions selected from calcium, sodium, potassium, magnesium and chloride and glucose in aqueous solution, said composition further including a fat graft effective number of autologous adipocytes within the range of about $5\times10^8$ to about $5\times10^{12}$ cells per ml of said medium.

2. The composition according to claim 1 further including adipocyte growth effective amounts of non-essential amino acids.

3. The composition according to claim 2 wherein said anabolic hormone is insulin at a concentration of about 500 ng/ml to about 100 ug/ml.

4. The composition according to claim 3 wherein said insulin is included at a concentration of about 500 ng/ml to about 5 ug/ml.

5. The composition according to claim 3 further including triiodothyronine or thyroxine.

6. The composition according to claim 5 wherein said triiodothyronine is included in an amount ranging from about 1.0 ng/ml to about 50 ng/ml.

7. The composition according to claim 5 wherein said thyroxine is included in an amount ranging from about 5 ng/ml to about 100 ng/ml.

8. The composition according to claim 1 further including growth hormone in an amount ranging from about 0.5 ng/ml to about 50 ng/ml.

9. The composition according to claim 5 further including growth hormone in an amount ranging from about 0.5 ng/ml to about 50 ng/ml.

10. The composition according to claim 7 further including growth hormone in an amount ranging from about 0.5 ng/ml to about 50 ng/ml.

11. The composition according to claim 2 wherein said nutrient medium is selected from the group consisting of F10, F12, RPMI 1640, BGJ Medium, Dulbecco's Modified Essential Medium, Yamane, IMEM-20, Glasgow Modification Eagle Medium, L-15, McCoy's 5A Medium, Medium 199, Medium 199 with Earle's salt base, Medium 199 with Hank's salt base, CMRL 1415, CMRL 1969, CMRL 1066, NCTC 135, MB 75261, MAB 8713, DM 145, Williams'G, Neuman & Tytell, Higuchi, MCDB 301, MCDB 202, MCDB 501, MCDB 401, MCDB 411, MDBC 153 and MCDB 105.

12. The composition according to claim 8 wherein said nutrient medium is selected from the group consisting of F10, F12, RPMI 1640, BGJ Medium, Dulbecco's Modified Essential Medium, Yamane, IMEM-20, Glasgow Modification Eagle Medium, L-15, McCoy's 5A Medium, Medium 199, Medium 199 with Earle's salt base, Medium 199 with Hank's salt base, CMRL 1415, CMRL 1969, CMRL 1066, NCTC 135, MB 75261, MAB 8713, DM 145, Williams'G, Neuman & Tytell, Higuchi, MCDB 301, MCDB 202, MCDB 501, MCDB 401, MCDB 411, MDBC 153 and MCDB 105.

13. The composition according to claim 2 further including an effective amount of a cellular growth factor or transforming factor selected from the group consisting of epithelial growth factor, transforming growth factor, platelet derived growth factor, insulin-like growth factor and mixtures, thereof.

14. A composition for use in autologous fat grafting procedures comprising an adipocyte growth effective amount of at least one anabolic hormone selected from insulin, triiodothyronine, thyroxine or mixtures thereof in combination with a nutrient medium selected from the group consisting of Minimum Essential Medium Eagle, F10, F12, RPMI 1640, BGJ Medium, Basal Medium Eagle, Dulbecco's Modified Eagle Medium, Minimum Essential Medium Eagle with Earle's salt base, Minimum Essential Medium Eagle with Hank's salt base, Minimum Essential Medium Eagle with non-essential amino acids, Yamane, IMEM-20, Glasgow Modification Eagle Medium, L-15, McCoy's 5A Medium, Medium 199, Medium 199 with Earle's salt base, Medium 199 with Hank's salt base, CMRL 1415, CMRL 1969, CMRL 1066, NCTC 135, MB 75261, MAB 8713, DM 145, Williams'G, Neuman & Tytell, Higuchi, MCDB 301, MCDB 202, MCDB 501, MCDB 401, MCDB 411, MDBC 153 and MCDB 105, said composition further including a fat graft effective number of autologous adiocytes within the range of about $5 \times 10^8$ to about $5 \times 10^{12}$ cells per ml of said medium.

15. The composition according to claim 14 wherein said anabolic hormone is insulin at a concentration of about 500 ng/ml to about 100 ug/ml.

16. The composition according to claim 15 further including triiodothyronine or thyroxine.

17. The composition according to claim 16 wherein said thyroxine is included in an amount ranging from about 5 ng/ml to about 100 ng/ml.

18. The composition according to claim 16 further including growth hormone in an amount ranging from about 0.5 ng/ml to about 50 ng/ml.

19. A method for treating tissue depressions or augmenting tissue in patients comprising injecting into said tissue a composition comprising an adipocyte growth effective amount of at least one anabolic hormone selected from insulin, triiodothyronine, thyroxine or mixtures thereof in combination with a nutrient medium comprising lipocyte growth effective amounts of essential amino acids, a mixture of vitamins comprising effective amounts of folate, niacinamide, pantothenate, pyridoxine, riboflavin and thiamin, a mixture of inorganic ions selected from calcium, sodium, potassium, magnesium and chloride and glucose in aqueous solution, said composition further including a fat graft effective amount of autologous adipocytes.

20. The method according to claim 19 wherein said anabolic hormone is insulin at a concentration of about 500 ng/ml to about 100 ug/ml.

21. The method according to claim 20 wherein said insulin is included at a concentration of about 500 ng/ml to about 5 ug/ml.

22. The method according to claim 20 further including triiodothyronine or thyroxine.

23. The method according to claim 22 wherein said triiodothyronine is included in an amount ranging from about 1.0 ng/ml to about 50 ng/ml.

24. The method according to claim 22 wherein said thyroxine is included in an amount ranging from about 5 ng/ml to about 100 ng/ml.

25. The method according to claim 19 further including growth hormone in an amount ranging from about 0.5 ng/ml to about 50 ng/ml.

26. The method according to claim 23 further including growth hormone in an amount ranging from about 0.5 ng/ml to about 50 ng/ml.

27. The method according to claim 24 further including growth hormone in an amount ranging from about 0.5 ng/ml to about 50 ng/ml.

28. The method according to claim 19 wherein said nutrient medium is selected from the group consisting of Minimum Essential Medium Eagle, Basal Medium Eagle, Dulbecco's Modified Eagle Medium, Minimum Essential Medium Eagle with Earle's salt base, Minimum Essential Medium Eagle with Hank's salt base, Minimum Essential Medium Eagle with non-essential amino acids, F10, F12, RPMI 1640, BGJ Medium, Dulbecco's Modified Essential Medium, Yamane, IMEM-20, Glasgow Modification Eagle Medium, L-15, McCoy's 5A Medium, Medium 199, Medium 199 with Earle's salt base, Medium 199 with Hank's salt base, CMRL 1415, CMRL 1969, CMRL 1066, NCTC 135, MB 75261, MAB 8713, DM 145, Williams'G, Neuman & Tytell, Higuchi, MCDB 301, MCDB 202, MCDB 501, MCDB 401, MCDB 411, MDBC 153 and MCDB 105.

29. The method according to claim 27 herein said nutrient medium is selected from the group consisting of Minimum Essential Medium Eagle, Basal Medium Eagle, Dulbecco's Modified Eagle Medium, Minimum Essential Medium Eagle with Earle's salt base, Minimum Essential Medium Eagle with Hank's salt base, Minimum Essential Medium Eagle with non-essential amino acids, F10, F12, RPMI 1640, BGJ Medium, Dulbecco's Modified Essential Medium, Yamane, IMEM-20, Glasgow Modification Eagle Medium, L-15, McCoy's 5A Medium, Medium 199, Medium 199 with Earle's salt base, Medium 199 with Hank's salt base, CMRL 1415, CMRL 1969, CMRL 1066, NCTC 135, MB 75261, MAB 8713, DM 145, Williams'G, Neuman & Tytell, Higuchi, MCDB 301, MCDB 202, MCDB 501, MCDB 401, MCDB 411, MDBC 153 and MCDB 105.

30. The method according to claim 29 wherein said nutrient medium is MCDB 105 or BJG medium.

31. The method according to claim 27 wherein said adipocytes are substantially separated from triglycerides, cell fragments, blood components, blood cells and large connective tissue fragments.

32. The method according to claim 19 further including an adipocyte growth effective amount of a cellular growth factor or transforming factor selected from the group consisting of epithelial growth factor, transforming growth factor, platelet derived growth factor, insulin-like growth factor and mixture, thereof.

33. A method for improving the engrafting of fat in an autologous fat graft procedure comprising utilizing in said fat graft procedure a composition comprising an adipocyte growth effective amount of at least one non-steroidal anabolic hormone selected from insulin, triiodothyronine, thyroxine or mixtures thereof, in combination with a nutrient medium comprising adipocyte growth effective amounts of essential amino acids, a mixture of vitamins comprising effective amounts of folate, niacinamide, pantothenate, pyridoxine, riboflavin and thiamin, a mixture of inorganic ions selected from calcium, sodium, potassium, magnesium and chloride and glucose in aqueous solution, said composition further including a fat graft effective amount of autologous adipocytes, said lipocytes being substantially separated from triglycerides, cell fragments, blood components, blood cells and large connective tissue fragments.

34. The method according to claim 33 wherein said composition further comprises an adipocyte growth effective amount of non-essential amino acids.

35. The method according to claim 34 wherein said anabolic hormone is insulin at a concentration of about 500 ng/ml to about 100 ug/ml.

36. The method according to claim 35 wherein said insulin is included at a concentration of about 500 ng/ml to about 5 ug/ml.

37. The method according to claim 35 further including triiodothyronine in an amount ranging from about 1.0 ng/ml to about 50 ng/ml or thyroxine in an amount ranging from about 5 ng/ml to about 100 ng/ml.

38. The method according to claim 34 further including growth hormone in an amount ranging from about 0.5 ng/ml to about 50 ng/ml.

39. The method according to claim 37 further including growth hormone in an amount ranging from about 0.5 ng/ml to about 50 ng/ml.

40. The method according to claim 33 wherein said nutrient medium is selected from the group consisting of Minimum Essential Medium Eagle, Basal Medium Eagle, Dulbecco's Modified Eagle Medium, Minimum Essential Medium Eagle with Earle's salt base, Minimum Essential Medium Eagle with Hank's salt base, Minimum Essential Medium Eagle with non-essential amino acids, F10, F12, RPMI 1640, BGJ Medium, Dulbecco's Modified Essential Medium, Yamane, IMEM-20, Glasgow Modification Eagle Medium, L-15, McCoy's 5A Medium, Medium 199, Medium 199 with Earle's salt base, Medium 199 with Hank's salt base, CMRL 1415, CMRL1969, CMRL 1066, NCTC 135, MB 75261, MAB 8713, DM 145, Williams'G, Neuman & Tytell, Higuchi, MCDB 301, MCDB 202, MCDB 501, MCDB 401, MCDB 411, MDBC 153 and MCDB 105.

41. The method according to claim 39 wherein said nutrient medium is selected from the group consisting of Minimum Essential Medium Eagle, Basal Medium Eagle, Dulbecco's Modified Eagle Medium, Minimum Essential Medium Eagle with Earle's salt base, Minimum Essential Medium Eagle with Hank's salt base, Minimum Essential Medium Eagle with non-essential amino acids, F10, F12, RPMI 1640, BGJ Medium, Dulbecco's Modified Essential Medium, Yamane, IMEM-20, Glasgow Modification Eagle Medium, L-15, McCoy's 5A Medium, Medium 199, Medium 199 with Earle's salt base, Medium 199 with Hank's salt base, CMRL 1415, CMRL 1969, CMRL 1066, NCTC 135, MB 75261, MAB 8713, DM 145, Williams'G, Neuman & Tytell, Higuchi, MCDB 301, MCDB 202, MCDB 501, MCDB 401, MCDB 411, MDBC 153 and MCDB 105.

42. The method according to claim 41 wherein said nutrient medium is MCDB 105 or BJG medium.

43. The method according to claim 33 further including an adipocyte growth effective amount of a cellular growth factor or transforming factor selected from the group consisting of epithelial growth factor, transforming growth factor, platelet derived growth factor, insulin-like growth factor and mixtures thereof.

44. A method for improving the engrafting of fat in an autologous fat graft procedure comprising utilizing in said fat graft procedure a composition comprising an adipocyte growth effective amount of a combination of insulin, human growth hormone and triiodothyronine or thyroxine in combination with a nutrient medium comprising adipocyte growth effective amounts of essential amino acids, non-essential amino acids, a mixture of vitamins comprising effective amounts of folate, niacinamide, pantothenate, pyridoxine, riboflavin and thiamin, a mixture of inorganic ions selected from calcium, sodium, potassium, magnesium and chloride and glucose in aqueous solution, said composition further including a fat graft effective amount of autologous adipocytes, said adipocytes being substantially separated from triglycerides, cell fragments, blood components, blood cells and large connective tissue fragments.

45. The method according to claim 44 wherein said insulin is included in said composition at a concentration ranging from about 500 ng/ml to about 100 ug/ml, said growth hormone is included in said composition at a concentration ranging from about 0.5 ng/ml to aobut 50 ng/ml and said triiodothyronine or thyroxine is included in said composition at a concentration ranging from about 1.0 ng/ml to about 100 ng/ml.

46. The method according to claim 45 wherein said medium is selected from the group consisting of F10, F12, RPMI 1640, BGJ Medium, Dulbecco's Modified Essential Medium, Yamane, IMEM-20, Glasgow Modification Eagle Medium, L-15, McCoy's 5A Medium, Medium 199, Medium 199 with Earle's salt base, Medium 199 with Hank's salt base, CMRL 1415, CMRL 1969, CMRL 1066, NCTC 135, MB 75261, MAB 8713, DM 145, Williams'G, Neuman & Tytell, Higuchi, MCDB 301, MCDB 202, MCDB 501, MCDB 401, MCDB 411, MDBC 153 and MCDB 105.

47. The method according to claim 44 wherein said nutrient medium is MCDB 105 or BJG medium.

* * * * *